United States Patent [19]

Oda et al.

[11] 4,067,321

[45] Jan. 10, 1978

[54] ELECTRODES FOR ELECTROENCEPHALOGRAPHIC EXAMINATIONS

[75] Inventors: Jun Oda, Chofu; Einosuke Koga, Tokyo; Shiro Endo, Chofu; Ichiro Aizawa; Kyoko Nishihara, both of Tokyo, all of Japan

[73] Assignee: Governor of Tokyo Metropolis, Japan

[21] Appl. No.: 701,045

[22] Filed: June 29, 1976

[51] Int. Cl.² .............................................. A61B 5/04
[52] U.S. Cl. ................................ 128/2.1 E; 128/418; 128/DIG. 4
[58] Field of Search ............... 128/2.06 E, 2.1 E, 404, 128/410, 411, 416, 417, 418, DIG. 4, 155, 156, 163

[56] References Cited

U.S. PATENT DOCUMENTS

| 990,158 | 4/1911 | Moses | 128/417 |
|---|---|---|---|
| 2,685,086 | 8/1954 | Henry | 128/155 X |
| 2,807,262 | 9/1957 | Lew | 128/156 |
| 2,872,926 | 2/1959 | Alderman | 128/410 |
| 3,092,103 | 6/1963 | Mower | 128/163 X |
| 3,151,619 | 10/1964 | Sullivan | 128/417 |
| 3,340,868 | 9/1967 | Darling | 128/2.06 E |
| 3,464,404 | 9/1969 | Mason | 128/2.06 E |
| 3,599,629 | 8/1971 | Gordy | 128/2.06 E |

FOREIGN PATENT DOCUMENTS

| 1,402,205 | 8/1975 | United Kingdom | 128/2.06 E |

Primary Examiner—John D. Yasko
Assistant Examiner—Lee S. Cohen
Attorney, Agent, or Firm—Cooper, Dunham, Clark, Griffin & Moran

[57] ABSTRACT

An electrode for electroencephalographic examinations which comprises a dish type metal electrode plate having mounted thereto at the peripheral edge an annular insulating plate with plural leg pieces extending radially outward therefrom. This electrode, when appropriately positioned on the human head, will stay steadily attached for a long period of time and will not be detached easily by the movement of the head.

6 Claims, 4 Drawing Figures

ELECTRODES FOR ELECTROENCEPHALOGRAPHIC EXAMINATIONS

BACKGROUND OF THE INVENTION

The present invention relates to an improvement in electrodes which are attached to the human head when the electroencephalographic examination is performed.

Electroencephalography is one of the electrophysiological methods to investigate biological phenomena. In general, electroencephalography is practiced by attaching electrodes to several positions on the skin of the head, connecting the lead wires extending from the electrodes to an electroencephalograph and observing the electroencephalographic patterns on the recorder.

Proposed hitherto as electrodes utilizable for this purpose are those of a dish type, those of a cup type, those of a strip type and those of a needle type. Generally, these electrodes do not involve any problem when used for a short-term examination but there are drawbacks when they are used for obtaining continuous recordings for a long period of time, for example, over 30 minutes or for obtaining a recording of the subject a state of motion where the head is moving, since these electrodes tend to be detached from the head skin, thus making it difficult to obtain exact results of the examination.

BRIEF SUMMARY OF THE INVENTION

Accordingly, it is an object of the present invention to provide an improved electrode for electroencephalography.

It is another object of the present invention to provide an electrode for electroencephalography which will not be detached from the head skin when used for a long period of time or when used on a head in the state of motion.

It is still another object of the present invention to provide an electrode for electroencephalography equipped with leg pieces to secure intimate contact of the electrode with the head skin.

Other objects and aspects of the invention will become apparent from the following description of embodiments with reference to the accompanying drawings in which.

DETAILED DESCRIPTION OF THE INVENTION

Figure 1:
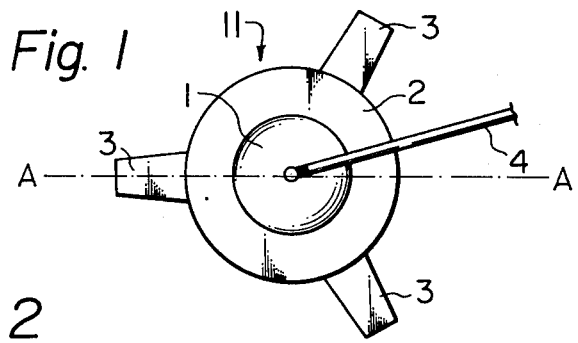
FIG. 1 is a plan view of an electrode of the present invention.
Figure 2:
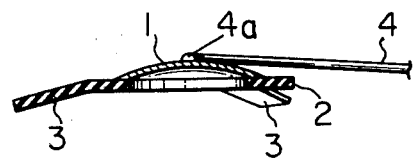
FIG. 2 is a cross sectional view of what is shown in FIG. 1 cut along the line A-A.

As is shown in an accompanying FIGS. 1 and 2, the electrode of the present invention comprises a dish type metal electrode plate 1; a lead wire 41 with one terminal connected to the electrode plate at around the center of the upper surface thereof and with its other terminal extending to an electroencephalograph; an annular insulating plate 2 mounted to the electrode plate at the peripheral edge thereof; and plural leg pieces 3, 3, . . . fitted to the annular insulating plate and extending outwardly in the radial direction from the center of the electrode plate.

The dish type metal electrode plate 1 is a dish type disk plate with a concave lower surface and made of a metal with good electric conductivity, such as gold, silver or copper. The electrode plate is usually 0.05-0.03 mm in thickness and 5-15 mm in diameter. A terminal 4a of a lead wire 4 is connected to the electrode plate near the center of the upper surface thereof by soldering, welding or the like means. The other terminal of the lead wire is connected to an electroencephalograph. The annular insulating plate is generally made of a synthetic resin such as a vinyl chloride resin, a polyamide resin or a polyester resin and has three or more leg pieces 3, 3 . . . molded integrally into a single piece with the annular insulating plate and extending outwardly in the radial direction from the center of the electrode plate. These leg pieces are slightly slanted downwardly from the insulating plate so that they may be brought into intimate contact with the head skin. The annular insulating plate is 0.2-1 mm in thickness and 10-20 mm in outer diameter. The length of each leg piece is 3-10 mm. The electrode plate and the annular insulating plate are firmly bonded to each other by the aid of an adhesive such as one of the epoxy series or acrylic series.

Figure 3:
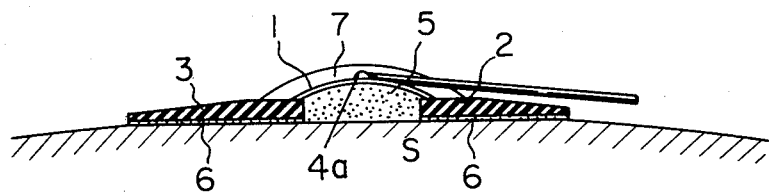
FIG. 3 is a cross sectional view of an electrode of the present invention in the state of being attached to the head skin.

As shown in FIG. 3, an electroencephalographic examination using the electrodes of the present invention is initiated by placing the electrode 1 the lower concave portion of which is filled with an electrode paste 5 on the cleaned skin of the head. An adhesive 6 such as a collodion is applied onto the lower surfaces of the insulating plate 2 and the leg piece 3, which are brought into contact with the head skin, and the plate and the leg pieces are then attached to the head skin. The electrode plate is then covered with an adhesive 7 of a synthetic resin series and dried by a drier.

Figure 4:
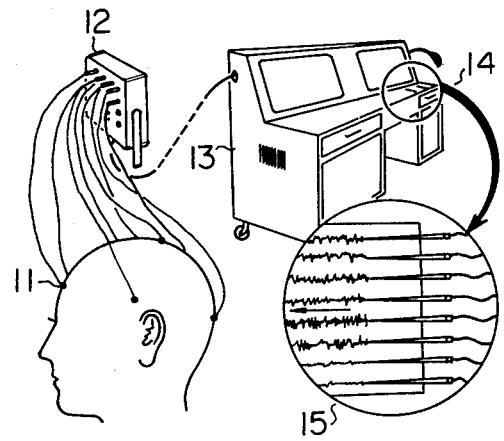
FIG. 4 is a pictorial view of conducting the recording of electroencephalograms with electrodes of the present invention.

Electroencephalography is carried out by attaching the electrodes 11 on a few places of the head skin in the above mentioned manner, as shown in FIG. 4, connecting the lead wires through an electrode box 12 to an electroencephalograph 13 and observing the data 15 recorded on a roll paper with a recorder 14.

The use of the electrode of the present invention brings about the following advantages in the course of electrocephalographic examinations.

As the electrode paste is sealed completely, it is not dried during the examination whereby the electrode resistance is maintained at a low level.

Since the contact area of the electrode with head skin is broad, strong and stable adhesion can be attained between them.

The leg pieces go between hair, thus serving to stabilize adhesion.

The subject can be examined comfortably for a long period of time. No injuries of head skin due to the electrodes themselves occur.

Attaching and detaching of the electrodes are easy and require much shorter time than the conventional ones.

What is claimed is:

1. An electrode for attachment to the head of a subject for electroencephalographic examinations which comprises:
   a dish-type metal electrode plate having an upper surface and a lower peripheral edge;
   a lead wire with one terminal connected to the electrode plate on the upper surface thereof and with its other terminal adapted to be connected to an electroencephalograph;

coating means for insulatingly covering the upper surface of said electrode plate and said one terminal;

an annular insulating plate mounted on the electrode plate at the lower peripheral edge thereof;

three elongated leg pieces fitted to the annular insulating plate and extending outwardly equiangularly in the radial direction from the center of the electrode and downwardly from said insulating plate for intimate contact with the head skin of the subject; and means for adhesively attaching said insulating plate and said elongated leg pieces to the head skin of the subject to produce stable adhesion of said electrode to the subject's head.

2. An electrode according to claim 1 wherein the dish type metal electrode plate is of a material from the group consisting of silver, gold, and copper.

3. An electrode according to claim 1 wherein the dish-type metal electrode plate has a concave lower surface which cooperates with said insulating plate to define a chamber for sealably accommodating electrode paste between said electrode and the head of a subject.

4. An electrode according to claim 1 wherein said terminal connected to the upper surface of the electrode plate is connected near the center thereof.

5. An electrode according to claim 1 wherein said insulating plate and said leg pieces are integrally constructed.

6. An electrode according to claim 1 wherein said coating means and said insulating plate cooperate to insulate said electrode plate externally of the head of a patient.

* * * * *